(12) United States Patent
Yan et al.

(10) Patent No.: US 11,017,529 B2
(45) Date of Patent: May 25, 2021

(54) METHOD FOR DETERMINING A CHARACTERISTIC BLOOD VALUE, COMPUTED TOMOGRAPHY DEVICE, COMPUTER PROGRAM AND ELECTRONICALLY READABLE STORAGE MEDIUM

(71) Applicant: Siemens Healthcare GmbH, Erlangen (DE)

(72) Inventors: Jing Yan, Shanghai (CN); Thomas Flohr, Uehlfeld (DE); Bernhard Schmidt, Fuerth (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 67 days.

(21) Appl. No.: 16/386,455

(22) Filed: Apr. 17, 2019

(65) Prior Publication Data
US 2019/0325575 A1 Oct. 24, 2019

(30) Foreign Application Priority Data
Apr. 20, 2018 (EP) .................... 18168505

(51) Int. Cl.
*G06T 7/00* (2017.01)
*G06T 7/11* (2017.01)
(Continued)

(52) U.S. Cl.
CPC ............ *G06T 7/0012* (2013.01); *A61B 6/481* (2013.01); *A61B 6/507* (2013.01); *G06K 9/0014* (2013.01);
(Continued)

(58) Field of Classification Search
CPC .................................................. G06T 7/0012
See application file for complete search history.

(56) References Cited

U.S. PATENT DOCUMENTS

| 2009/0208084 A1 | 8/2009 | Liu et al. |
| 2012/0039943 A1* | 2/2012 | Harrop .................... A61P 37/04 424/277.1 |

(Continued)

OTHER PUBLICATIONS

X. Liu et al., "Quantitative imaging of element composition and mass fraction using dual-energy CT: Three-material decomposition", Med. Phys. 36 (5), May 2009, pp. 1602-1609; 2009.
(Continued)

*Primary Examiner* — Oneal R Mistry
(74) *Attorney, Agent, or Firm* — Harness, Dickey & Pierce, P.L.C.

(57) ABSTRACT

A method is for determining at least one first characteristic value of blood in a patient. In an embodiment, the method includes acquiring, via a computed tomography device, computed tomography data of the patient for at least two energy levels of radiation using multi-energy computed tomography; defining a region of interest including blood, in at least one image data set reconstructed from the computed tomography data acquired; determining, at least in the region of interest defined, attenuation coefficients for each energy level of the at least two energy levels; performing material decomposition into at least two materials, one material of the two materials being iron, using the attenuation coefficients determined, yielding at least a fraction of iron in the region of interest defined; and determining the at least one first characteristic value, at least one of as and from the fraction of iron yielded.

19 Claims, 3 Drawing Sheets

(51) Int. Cl.
| | |
|---|---|
| *G16H 30/40* | (2018.01) |
| *A61B 6/00* | (2006.01) |
| *G06K 9/00* | (2006.01) |
| *G06K 9/20* | (2006.01) |
| *G06T 11/00* | (2006.01) |

(52) U.S. Cl.
CPC .............. *G06K 9/2054* (2013.01); *G06T 7/11* (2017.01); *G06T 11/008* (2013.01); *G16H 30/40* (2018.01); *G06T 2207/10081* (2013.01); *G06T 2207/10116* (2013.01); *G06T 2207/30024* (2013.01)

(56) References Cited

U.S. PATENT DOCUMENTS

| | | | | |
|---|---|---|---|---|
| 2015/0037250 A1* | 2/2015 | Yamagata | .......... | A61K 49/0002 424/1.29 |
| 2015/0038827 A1* | 2/2015 | Yamagata | .............. | A61B 6/481 600/411 |
| 2015/0348289 A1* | 12/2015 | Ida | .......... | A61B 6/032 382/131 |
| 2018/0068464 A1 | 3/2018 | Gronberg et al. | | |
| 2018/0249979 A1* | 9/2018 | Wang | ..................... | A61B 6/035 |
| 2018/0321347 A1* | 11/2018 | Wang | ..................... | A61B 5/055 |

OTHER PUBLICATIONS

Jing Ma et al: "Separation of Hepatic Iron and Fat by Dual-Source Dual-Energy Computed Tomography Based on Material Decomposition: An Animal Study"; PLOS One; vol. 9. No. 10; pp. 1-6; e110964; XP055506997.

Wu Xingwang et al: "A study of CT monochromatic imaging for quantitative detecting hemoglobin levels"; Journal of X-Ray Science and Technology; vol. 20 No. 4; pp. 483-488; XP009508095; ISSN: 1095-9114; DOI: 10.3233/XST-2012-00354.

Ting Su et al: "A spectral X-ray CT simulation study for quantitative determination of iron"; Nuclear Instruments & Methods in Physics Research. Section A; vol. 894; pp. 39-46; XP055507390; NL; ISSN: 0168-9002; DOI:10.1016/j.nima.2018.03.043.

Extended European Search Report (EPO form 1507N) for European Appln No. 181685058 dated Sep. 27, 2018.

* cited by examiner

METHOD FOR DETERMINING A CHARACTERISTIC BLOOD VALUE, COMPUTED TOMOGRAPHY DEVICE, COMPUTER PROGRAM AND ELECTRONICALLY READABLE STORAGE MEDIUM

The present application hereby claims priority under 35 U.S.C. § 119 to European patent application number EP 18168505.8 filed Apr. 20, 2018, the entire contents of which are hereby incorporated herein by reference.

FIELD

Embodiments of the invention generally relate to a method for determining at least one first characteristic value of blood in a patient, the at least one first characteristic value describing the iron content of the blood; a computed tomography device; a computer program and an electronically readable storage medium.

BACKGROUND

The analysis of human blood is a valuable tool in diagnosing patients in healthcare. An important object of such examinations is the haemoglobin content in the blood. Haemoglobin enables the transport of oxygen from the lungs to organs or muscles. Iron ions are establishing the binding of oxygen with the haemoglobin complex, leading to a change in the colour of the blood from dark red to light red and enabling the transport of oxygen.

Due to the importance of this mechanism, physicians are interested in characteristic values of the blood describing the amount of iron load in the erythrocytes. Another characteristic value of blood describes the blood composition regarding blood plasma and erythrocytes. Known, often used characteristic values are the haematocrit and MCH (Mean Corpuscular/Cellular Haemoglobin). While the haematocrit is defined as the proportion of blood volume occupied by wet blood cells, the mean corpuscular haemoglobin is the average mass of haemoglobin per red blood cell in a sample of blood.

To obtain such (and other) characteristic values of blood, a blood draw is typically taken and analysed in a laboratory. This process takes additional time and effort and is an additional step in a busy clinical environment.

SUMMARY

At least one embodiment of the present invention is directed to a method and apparatus for determining characteristic values of blood relating to the iron content, in particular while being embedded in another examination.

Embodiments of the present invention are directed to a method, a computed tomography device, a computer program and an electronically readable storage medium.

In a method for determining at least one first characteristic value of blood in a patient, the at least one first characteristic value describing the iron content of the blood, according to at least one embodiment of the invention, the method comprising:

acquiring, via a computed tomography device, computed tomography data of the patient for at least two energy levels of radiation using multi energy computed tomography;

defining a region of interest including blood, in at least one image data set reconstructed from the computed tomography data acquired;

determining, at least in the region of interest defined, attenuation coefficients for each energy level of the at least two energy levels;

performing material decomposition into at least two materials, one material of the two materials being iron, using the attenuation coefficients determined, yielding at least a fraction of iron in the region of interest defined; and determining the at least one first characteristic value, at least one of as and from the fraction of iron yielded.

At least one embodiment of the invention further concerns a computed tomography device, comprising at least one acquisition arrangement having an x-ray source and an x-ray detector, in particular a photon counting detector, and a control device configured to perform a method according to at least one embodiment of the invention. All comments and features discussed regarding embodiments of the inventive method may be applied accordingly to the computed tomography device, such that the same advantages are achieved.

In at least one embodiment, the control device may comprise a processor and a memory. In particular, the control device may comprise an acquisition unit and a reconstruction unit as known from the state of the art to control the acquisition arrangement to acquire computed tomography data and to reconstruct image data sets and/or attenuation coefficients from the computed tomography data. These units can also be used to perform the method according to an embodiment of the invention. Additionally, the control device may comprise a region of interest (ROI) definition unit for defining the region of interest, a material decomposition unit and a characteristic value determination unit. Please note that at least the steps of reconstruction, material decomposition and characteristic value determination are performed completely automatically.

A computer program according to at least one embodiment of the invention can be loaded directly into a memory of a control device of a computed tomography device and comprises program segments/modules to perform the steps of a method according to at least one embodiment of the invention when the computer program is executed in the control device of the computed tomography device. The computer program according to at least one embodiment of the invention may be stored on an electronically readable storage medium according to at least one embodiment of the invention, which thus comprises electronically readable control information stored thereon, wherein the control information comprises at least one computer program according to at least one embodiment of the invention and is configured to perform the steps of a method according to at least one embodiment of the invention when the storage medium is used in a control device of a computed tomography device. At least one embodiment of the inventive electronically readable storage medium may be a non-transitional medium, for example a CD-ROM.

BRIEF DESCRIPTION OF THE DRAWINGS

Further details and advantages of the present invention can be taken from the following description of preferred embodiments taken in conjunction with the drawings, in which.

DETAILED DESCRIPTION OF THE EXAMPLE EMBODIMENTS

Figure 1:
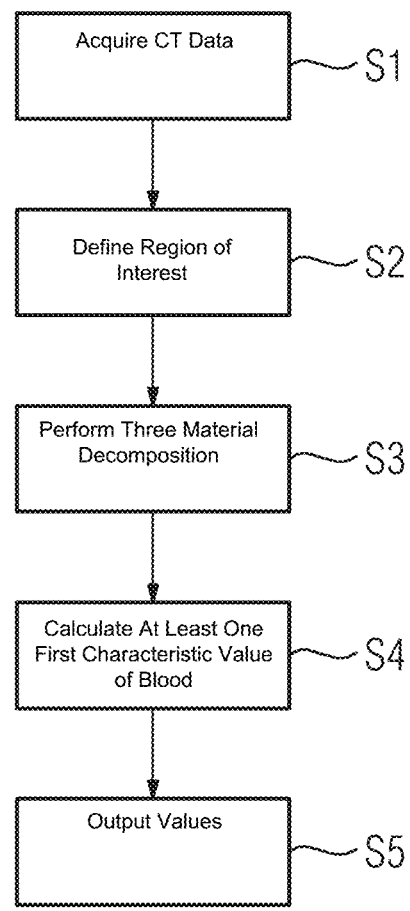
FIG. 1 is a flow chart of an embodiment of the method according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

In a method for determining at least one first characteristic value of blood in a patient, the at least one first characteristic value describing the iron content of the blood, according to at least one embodiment of the invention, in a computed tomography device, computed tomography data of the patient for at least two energy levels of radiation is acquired using multi energy computed tomography, a region of interest comprising blood is defined in at least one image data set reconstructed from the computed tomography data, at least in the region of interest, attenuation coefficients for at least the region of interest are determined for each energy level, material decomposition into at least two materials, one material being iron, is performed using the attenuation coefficients, yielding at least a fraction of iron in the region of interest, and the first characteristic value is determined as and/or from the iron fraction.

It is thus proposed, in at least one embodiment, to derive the amount of iron load in erythrocytes and optionally other values, in particular the contribution of blood plasma, by spectral computed tomography (CT) methods. Single energy computed tomography techniques cannot be used to derive information on iron content in blood, since both density differences and material changes impact measured computed tomography values and thus these effects cannot be separated by single energy computed tomography.

However, in contrast to iron, blood plasma and also erythrocytes (excluding the iron) have only a negligible spectral behaviour. This allows iron to be separated from the other components of erythrocytes and generally blood. In this context, it is noted that, for example, contrast agents or other material supplying other high atomic number substances into the blood should not be used while acquiring the computed tomography data.

Spectral material decomposition is already well-known in the state of the art, but has never been proposed regarding blood analysis. By performing the material decomposition proposed, the amount of iron in blood, for example in milligram per $cm^3$, can be quantified and the iron load determined. This valuable information can be derived automatically from spectral CT data. Anaemia, which may be caused by a low amount of iron, or the temporary change of iron overload, for example due to a blood transfusion, can be monitored and quantified by using the inventive method.

Advantageously, the computed tomography data may also be analysed to derive other diagnostically valuable information. In other words, the determination of the first characteristic value of blood in a patient as described here can be added to any multi energy computed tomography examination of a patient serving any purpose, as long as a region of interest comprising blood is imaged and the blood does not contain any other material of a high atomic number, for example a iodine contrast agent. The imaging examination of the patient and the blood analysis regarding iron can thus be performed in "one go", obviating the need for a blood draw and a laboratory analysis.

The region of interest may be determined at least partly manually and/or at least partly automatically, in particular using a segmentation algorithm. Most computed tomography examinations include at least one major blood vessel, such that a region of interest containing only blood can be defined in reconstructed computed tomography image data sets. While it is, of course, possible, to manually define such a region of interest, for example by viewing the image data set and marking a suitable region of interest, methods for automatically supporting a user in locating the blood or to even fully automatically define a region of interest containing only blood have also been proposed in the state of the art. These methods can also be applied here. For example, automatic segmentation algorithms may be used to assist the user, who may have provided a starting point, or to fully manually detect blood vessels in the imaged region. Additionally or alternatively, matching algorithms using anatomic atlases may be used.

In particular, the region of interest may be chosen as a part of a major blood vessel, in particular the aorta. Most CT examinations regarding the torso of the patient depict at least part of a major blood vessel, in particular the aorta, such that a suitable region of interest may be defined.

In a first embodiment of the invention, a two material decomposition is performed, the other material comprising both blood plasma and erythrocytes (excluding iron). This already provides useful information, in particular regarding anaemia and other diseases directly relating to iron content in the blood.

However, in an especially preferred embodiment, a three material decomposition is performed, wherein the other two materials are blood plasma and erythrocytes (excluding iron). In addition to the quantification of the amount of iron in the blood, further analysis of the blood plasma/non-iron erythrocytes part of the blood allows for quantifications of further characteristic values. In particular, at least one second characteristic value of blood is determined from the fractions of blood plasma and erythrocytes yielded from the three material decomposition, such that the volume and/or mask contributions of blood plasma and erythrocytes can be quantified. In a concrete embodiment, one of the at least one second characteristic value may be the haematocrit value.

Methods and algorithms for a three material decomposition have already been proposed in the state of the art. In these methods, it is usually assumed that volumes are conserved even in the case of a mixture of the materials concerned. In US 2009/0208084 A1, the entire contents of which are hereby incorporated herein by reference, Liu et al. propose to use the principle of mass conservation instead, assuming that the sum of masses of the three constituent materials is equivalent to the mass of the mixture, as also described in X. Liu et al., "Quantitative imaging of element composition and mass fraction using dual-energy CT: Three-material decomposition", Med. Phys. 36 (5), May 2009, pages 1602-1609, the entire contents of which are hereby incorporated herein by reference. While such algorithms may also be applied in the method according to the invention, other approaches for three-material decomposition may also be used.

In a preferred embodiment, it is assumed that blood plasma and erythrocytes (excluding iron) have a comparable spectral behaviour, wherein the respective fractions are calculated in the space spanned by the attenuation values at the two energy levels by projecting a measured point along an iodine direction onto a line connecting a pure blood plasma point and a pure erythrocytes (excluding iron) point and determining the fractions according to the projected point dividing the line. Measured points, i.e. the attenuation coefficients (in particular HU values) of voxels in the region of interest, may be plotted into a diagram, one axis denoting the attenuation coefficients according to the lower energy level, the other axis denoting the attenuation coefficients according to the higher energy level. Since the attenuation values of pure blood plasma and pure erythrocytes (neglecting the contribution of any iron, of course) are known for both energy levels, also respective reference points, i.e. a pure blood plasma point and a pure erythrocytes point, are also known in such a plot.

Assuming a comparable spectral behaviour, mixtures of pure blood plasma and pure erythrocytes (excluding iron) should have measurement points on a line connecting these two reference points, wherein the positions along the line describe the fractions of the respective materials. Taking iron into account, this means that a measurement point of a mixture containing iron, blood plasma and erythrocytes (excluding iron) may be projected onto this line along an iron direction (i.e. the direction of the pure iron reference point), wherein the distance along the iron direction between the measurement point and the projected point describes the iron content. Additionally, the position of the projected point on the line connecting the reference points describes the fraction of each of blood plasma and erythrocytes (excluding iron), in particular by dividing the length of the respective divisions of the line by the length of the whole line. Thus, based on the actual measured attenuation coefficients, a mixing coefficient and thus a percentage distribution of blood plasma and erythrocytes can be determined.

From a clinical perspective, it is extremely valuable to determine the at least one second characteristic value in addition to the first characteristic value, since a limited transport of oxygen can be a consequence of a reduced haematocrit value (small percentage of blood cells, e.g. indication for bleeding) or a problem with iron load in the erythrocytes itself, which would also lead to a limited efficiency in binding oxygen to the haemoglobin complex (refer to anulocytes).

Preferably, one of the at least one first characteristic value is a mean corpuscular haemoglobin value (MCH). Of course, also other first characteristic values may be used, in particular an iron concentration.

As has already been mentioned, the method according to the invention may also be used to derive trend information regarding the characteristic value or characteristic values. In particular, the first characteristic value of blood may be determined in at least two measurements separated in time to determine the trend information. In this manner, reactions to blood transfusions may be monitored and/or a disease process regarding to anaemia may be observed.

Preferably, a photon counting detector is used to acquire the computed tomography data. In photon counting detectors, detected photons may be sorted by energy to produce results according to different energy levels without having to use multiple x-ray sources and/or successive measurements. A broad spectrum may instead be used to illuminate the imaging region, since the energy separation takes place in the photon counting detector. In this manner, computed tomography data for at least two energy levels are acquired.

At least one embodiment of the invention further concerns a computed tomography device, comprising at least one acquisition arrangement having an x-ray source and an x-ray detector, in particular a photon counting detector, and a control device configured to perform a method according to at least one embodiment of the invention. All comments and features discussed regarding embodiments of the inventive method may be applied accordingly to the computed tomography device, such that the same advantages are achieved.

In at least one embodiment, the control device may comprise a processor and a memory. In particular, the control device may comprise an acquisition unit and a reconstruction unit as known from the state of the art to control the acquisition arrangement to acquire computed tomography data and to reconstruct image data sets and/or attenuation coefficients from the computed tomography data. These units can also be used to perform the method according to at least one embodiment of the invention. Additionally, the control device may comprise a region of interest (ROI) definition unit for defining the region of interest, a material decomposition unit and a characteristic value determination unit. Please note that at least the steps of reconstruction, material decomposition and characteristic value determination are performed completely automatically.

A computer program according to at least one embodiment of the invention can be loaded directly into a memory of a control device of a computed tomography device and comprises program segments/modules to perform the steps of a method according to at least one embodiment of the invention when the computer program is executed in the control device of the computed tomography device. The computer program according to at least one embodiment of the invention may be stored on an electronically readable storage medium according to at least one embodiment of the invention, which thus comprises electronically readable control information stored thereon, wherein the control information comprises at least one computer program according to at least one embodiment of the invention and is configured to perform the steps of a method according to at least one embodiment of the invention when the storage medium is used in a control device of a computed tomography device. At least one embodiment of the inventive electronically readable storage medium may be a non-transitional medium, for example a CD-ROM.

FIG. 1 is a flow chart of an embodiment of the present invention, which is integrated into an examination process of a patient, meaning that the computed tomography data discussed below are evaluated in a typical imaging application and additionally, as described in this embodiment, to determine characteristic values of blood of the patient.

In step S1, computed tomography data of an imaging region of the patient, in this case the upper torso, are acquired using a computed tomography device, in this case having a photon counting detector, such that one subset of the computed tomography data is associated with a lower energy level, for example corresponding to a certain tube voltage, and a second subset of a computed tomography data are associated with a higher, second energy level, for example corresponding to another tube voltage. In summary, dual energy computed tomography is performed.

In a step S2, a region of interest containing blood is defined after at least one image data set is reconstructed from the computed tomography data. Please note that the at least one image data set may already contain attenuation coefficients as image information, in particular as Hounsfield units (HU).

In this case, the region of interest is defined as a part of the aorta as a major blood vessel. The definition can be performed manually and/or automatically, in particular assisted. For example, the image data set can be displayed to a physician, who marks a region of interest in the aorta, in particular assisted by segmentation and/or annotation algorithms. However, the definition of the region of interest in step S2 may also be performed manually, in particular by using a segmentation algorithm and/or an anatomical atlas matching algorithm.

In a step S3, attenuation coefficients in the region of interest, which may already be available in the image data sets or are additionally reconstructed, for both energy levels are evaluated to perform a three material decomposition, wherein one material is iron, a second material is blood plasma and a third material is erythrocytes without their iron content (which is already the first material). As attenuation coefficients, in this embodiment, Hounsfield units (HU) are used.

Figure 2:
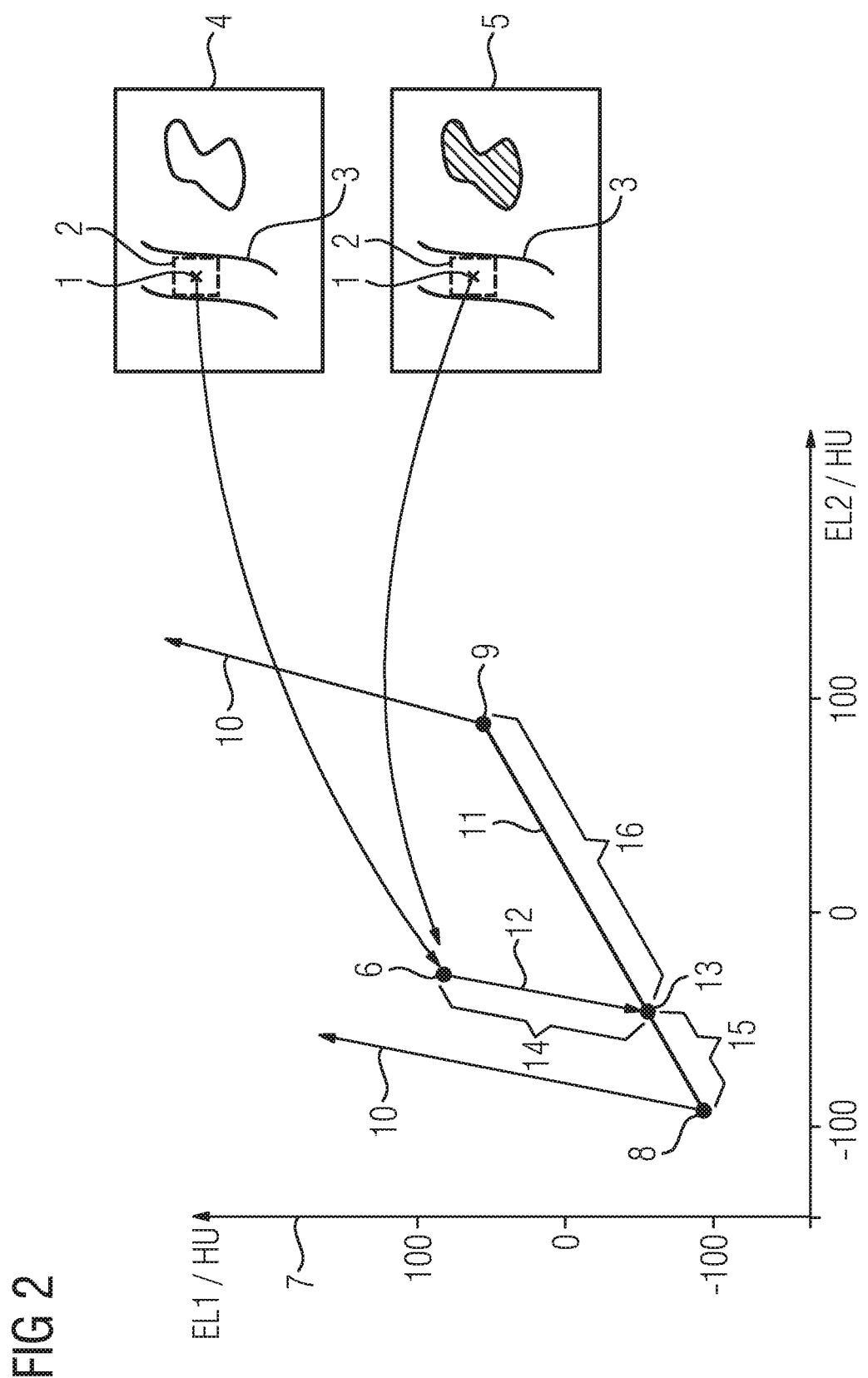
FIG. 2 shows the determination of fractions in a three material decomposition.

The three material decomposition process used is further illustrated in FIG. 2 for a voxel 1 of the region of interest 2 of the aorta 3, which is shown schematically in a high energy level attenuation coefficient image 4 and a low energy level attenuation coefficient image 5. The attenuation coefficients of both images 4, 5 for the voxel 1 define a measurement point 6 in a corresponding diagram 7, wherein attenuation coefficients of the energy levels are plotted on corresponding axis.

The diagram 7 of FIG. 2 also shows two reference points, namely a pure blood plasma point 8 corresponding to the attenuation coefficients of pure blood plasma and a pure erythrocytes point 9 corresponding to the attenuation coefficients of pure erythrocytes (excluding iron). A corresponding reference point for iron is far off above these reference points 8, 9, such that only the corresponding iron direction 10 is indicated.

Since the spectral behaviour of blood plasma and erythrocytes is assumed to be comparable, all measurement points for mixtures of pure blood plasma and pure erythrocytes should lie on a line 11 connecting the reference points 8, 9.

If the measurement point 6 corresponding to one of the voxels 1 in the region of interest 2 is projected onto the line 11 along the iron direction 10, as indicated by arrow 12, a projected point 13 on the line 11 results.

The fraction of iron in the voxel 1 is then quantified by the distance 14 between the measurement point 6 and the projected point 13, while the fractions of blood plasma and erythrocytes are quantified by the parts 15, 16 of the line 11 defined by the projected point 13.

To evaluate the whole region of interest 2, the results 14, 15 and 16 may be determined for each voxel 1 in the region of interest 2, whereafter these results may be statistically averaged. In another embodiment, it is also possible to use a statistical mean of all attenuation coefficients inside the volume of interest 2.

In a step S4, the results according to distance 14 and parts 15 and 16 are used to calculate at least one first characteristic value of the blood of the patient, describing the iron content of the blood, and at least one second characteristic value of the blood, describing the fraction of erythrocytes. In this case, an iron concentration is calculated as the first characteristic value and the haematocrit value is calculated as the second characteristic value.

In a step S5, the characteristic values of the blood are output to a user.

The steps S1 to S5 may be repeated at a later time to derive trend information regarding the characteristic values.

It is noted that it is also possible to only perform a two material decomposition, one material being iron, the other material comprising blood plasma and erythrocytes (excluding iron), such that only a first characteristic value of the blood can be calculated. Such an embodiment is, however, less preferred.

Figure 3:
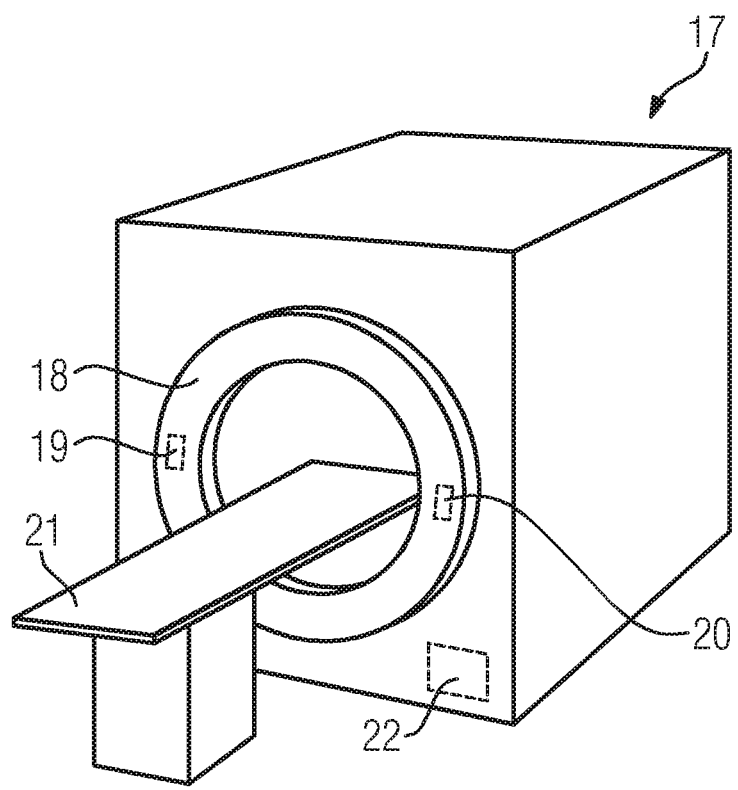
FIG. 3 shows a computed tomography device according to an embodiment of the invention.

FIG. 3 shows a schematic drawing of a computed tomography device 17 according to an embodiment of the invention. The computed tomography device 17 comprises a gantry 18, wherein an acquisition arrangement comprising an x-ray source 19 and an x-ray detector 20, in this case a photon counting detector, are rotated. A patient can be placed inside the gantry using a patient table 21. The computed tomography device 17 may also have additional acquisition arrangements rotatable in the gantry 18, in particular at a 90° angle to the shown acquisition arrangement.

The computed tomography device 17 is controlled by a control device 22, which is also configured to perform a method according to an embodiment of the invention. To this end, the control device may comprise an acquisition unit, a reconstruction unit, a region of interest definition unit, a material decomposition unit and a characteristic value determination unit.

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining at least one first characteristic value of blood in a patient, the at least one first characteristic value describing iron content of the blood, the method comprising:

acquiring, via a computed tomography device, computer tomography data of the patient for at least two energy levels of radiation using multi-energy computed tomography;

defining a region of interest in at least one image data set reconstructed from the acquired computed tomography data, the region of interest including the blood;

performing material decomposition into at least two materials using the determined attenuation coefficients to obtain at least a fraction of iron in the blood of the defined region of interest, one material of the at least two materials being iron; and determining the at least one first characteristic value based on the fraction of iron.

2. The method of claim 1, wherein the defining the region of interest defines the region of interest at least one of at least partly manually and at least partly automatically.

3. The method of claim 1, wherein the defining the region of interest defines the region of interest as a part of a blood vessel.

4. The method of claim 1, wherein the at least two materials includes both blood plasma and erythrocytes.

5. The method of claim 1, wherein the at least two materials include three materials and the performing the material decomposition includes, performing a three material decomposition, another of the at least two materials includes blood plasma and erythrocytes.

6. The method of claim 5, further comprising:

determining at least one second characteristic value of blood from at least one of a fraction of blood plasma obtained from the three material decomposition and a fraction of erythrocytes obtained from the three material decomposition.

7. The method of claim 6, wherein one of the at least one second characteristic value is a haematocrit value.

8. The method of claim 6, wherein the blood plasma and the erythrocytes are assigned a comparable spectral behaviour and the performing a three material decomposition includes, calculating the fraction of blood plasma and the fraction of erythrocytes in a space spanned by attenuation values at the at least two energy levels by projecting a measured point along an iron direction onto a line connecting a pure blood plasma point and a pure erythrocytes point and determining the fraction of blood plasma and the fraction of erythrocytes according to the projected measured point, the projected measured point dividing the line.

9. The method of claim 1, wherein one of the at least one first characteristic value is a mean corpuscular haemoglobin value.

10. The method of claim 1, wherein the determining determines the at least one first characteristic value in at least two measurements separated in time and determines a trend information.

11. The method of claim 1, wherein the acquiring includes using a photon counting detector to acquire the computed tomography data.

12. A computed tomography device, comprising:

at least one acquisition arrangement including an x-ray source and an x-ray detector; and a control device, configured to determine at least one first characteristic value of blood in a patient, the at least one first characteristic value describing iron content of the blood, by at least:

acquiring, via a computed tomography device, computed tomography data of the patient for at least two energy levels of radiation using multi-energy computed tomography;

defining a region of interest, in at least one image data set reconstructed from the acquired computed tomography data, the region of interest including the blood, determining attenuation coefficients for each energy level of the at least two energy levels in at least the defined region of interest, performing material decomposition into at least two materials using the determined attenuation coefficients to obtain at least a fraction of iron in the blood of the defined region of interest, one material of the at least two materials being iron, and determining the at least one first characteristic value based on the fraction of iron.

13. A non-transitory computer readable medium storing a computer program which, when the computer program is executed in a control device of a computed tomography device, is configured to perform the method of claim 1.

14. A non-transitory electronically readable storage medium, storing a computer program which, when the computer program is executed in a control device of a computed tomography device, is configured to perform the method of claim 1.

15. The method of claim 2, wherein the defining the region of interest defines the region of interest using a segmentation algorithm.

16. The method of claim 3, wherein the defining the region of interest defines the region of interest as a part of an aorta.

17. The method of claim 4, wherein the acquiring includes using a photon counting detector to acquire the computed tomography data.

18. The method of claim 5, wherein the acquiring includes using a photon counting detector to acquire the computed tomography data.

19. The computed tomography device of claim 12, wherein the x-ray detector is a photon counting detector.

* * * * *